United States Patent
Zhan et al.

(10) Patent No.: US 11,882,889 B2
(45) Date of Patent: Jan. 30, 2024

(54) FAULT-TOLERANT GRID FREQUENCY MEASUREMENT ALGORITHM DURING TRANSIENTS

(71) Applicant: UT-Battelle, LLC, Oak Ridge, TN (US)

(72) Inventors: Lingwei Zhan, Oak Ridge, TN (US); Thomas J. King, Jr., Oak Ridge, TN (US); Fuhua Li, Oak Ridge, TN (US); Yilu Liu, Oak Ridge, TN (US); Wenxuan Yao, Oak Ridge, TN (US); He Yin, Oak Ridge, TN (US); Bailu Xiao, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 255 days.

(21) Appl. No.: 17/204,494

(22) Filed: Mar. 17, 2021

(65) Prior Publication Data

US 2021/0328431 A1  Oct. 21, 2021

Related U.S. Application Data

(60) Provisional application No. 63/010,863, filed on Apr. 16, 2020.

(51) Int. Cl.
*A41D 13/11* (2006.01)
*A61B 5/01* (2006.01)
(Continued)

(52) U.S. Cl.
CPC ........... *A41D 13/1184* (2013.01); *A61B 5/01* (2013.01); *A61F 9/045* (2013.01); *H02J 3/003* (2020.01);
(Continued)

(58) Field of Classification Search
CPC .. H02J 3/003; H02J 3/004; H02J 3/144; H02J 3/46; G06F 17/14
See application file for complete search history.

(56) References Cited

U.S. PATENT DOCUMENTS

| | | | | |
|---|---|---|---|---|
| 4,319,329 A | * | 3/1982 | Girgis | G01R 23/02 324/76.74 |
| 2010/0161263 A1 | * | 6/2010 | Benmouyal | G01R 19/2513 702/75 |

(Continued)

OTHER PUBLICATIONS

A. J. Roscoe, B. Dickerson and K. E. Martin, "Filter Design Masks for C37.118.1a-Compliant Frequency-Tracking and Fixed-Filter M-Class Phasor Measurement Units," in IEEE Transactions on Instrumentation and Measurement, vol. 64, No. 8, pp. 2096-2107, Aug. 2015.

(Continued)

*Primary Examiner* — Mohammad Ali
*Assistant Examiner* — Dhruvkumar Patel
(74) *Attorney, Agent, or Firm* — LEMPIA SUMMERFIELD KATZ LLC

(57) ABSTRACT

A system determines the frequency of grid signals corresponding to an electrical grid in real time. The system includes a transient detector that monitors a grid signal from a voltage meter or a current meter connected to the electrical grid. The system produces, in real time and at a sampling rate, a deviation signal indicative of a periodicity of the monitored grid signal. The system determines, over one or more cycles of the monitored grid signal, a measurement signal corresponding to the deviation signal. The system determines a frequency signal that corresponds a frequency estimation of the monitored signal by applying a frequency estimation when values of the measurement signal are less than a deviation threshold and maintaining the frequency (Continued)

signal at a constant value when values of the measured signal equal or exceeds the deviation threshold.

10 Claims, 7 Drawing Sheets

(51) Int. Cl.
*A61F 9/04* (2006.01)
*H02J 3/00* (2006.01)
*H02J 3/14* (2006.01)
*H02J 3/46* (2006.01)
*A42B 3/22* (2006.01)
*G06F 17/14* (2006.01)

(52) U.S. Cl.
CPC .............. *H02J 3/004* (2020.01); *H02J 3/144* (2020.01); *H02J 3/46* (2013.01); *A42B 3/225* (2013.01); *G06F 17/14* (2013.01)

(56) References Cited

U.S. PATENT DOCUMENTS

| | | | | |
|---|---|---|---|---|
| 2011/0153236 A1* | 6/2011 | Montreuil | ............ | G01R 31/088 |
| | | | | 702/58 |
| 2012/0175876 A1* | 7/2012 | Pendray | .................. | F02D 29/06 |
| | | | | 290/41 |
| 2013/0158901 A1* | 6/2013 | Sahinoglu | .............. | G01R 29/16 |
| | | | | 702/58 |
| 2013/0158903 A1* | 6/2013 | Sahinoglu | .......... | G01R 19/2513 |
| | | | | 702/58 |
| 2013/0169309 A1* | 7/2013 | Bickel | .................... | H02J 3/241 |
| | | | | 324/764.01 |
| 2013/0221977 A1* | 8/2013 | Ukil | ....................... | H02H 3/081 |
| | | | | 324/522 |
| 2017/0146577 A1* | 5/2017 | Kasztenny | ............. | H01H 47/00 |
| 2018/0316175 A1* | 11/2018 | Gubba Ravikumar | .. | H02H 3/46 |
| 2019/0173285 A1* | 6/2019 | Schneider | ............... | H02J 3/381 |

OTHER PUBLICATIONS

I. Kamwa, S. R. Samantaray, and G. Joos, "Compliance analysis of PMU algorithms and devices for wide-area stabilizing control of large power systems," IEEE Trans. Power Syst., vol. 28, No. 2, pp. 1766-1778, May 2013.

L. Zhan and Y. Liu, "Improved WLS-TF algorithm for dynamic synchronized angle and frequency estimation," in Proc. IEEE Power Energy Soc. Gen. Meeting, National Harbor, MD, USA, 2014, pp. 1-5.

L. Zhan, Y. Liu and Y. Liu, "A Clarke Transformation-Based DFT Phasor and Frequency Algorithm for Wide Frequency Range," in IEEE Transactions on Smart Grid, vol. 9, No. 1, pp. 67-77, Jan. 2018.

L. Zhan, Y. Liu, J. Culliss, J. Zhao and Y. Liu, "Dynamic Single-Phase Synchronized Phase and Frequency Estimation at the Distribution Level," in IEEE Transactions on Smart Grid, vol. 6, No. 4, pp. 2013-2022, Jul. 2015.

T. Xia and Y. Liu, "Single-phase phase angle measurements in electric power systems," IEEE Trans. Power Syst., vol. 25, No. 2, pp. 844-852, May 2010.

\* cited by examiner

FAULT-TOLERANT GRID FREQUENCY MEASUREMENT ALGORITHM DURING TRANSIENTS

RELATED APPLICATION

This application claims the benefit of priority of U.S. Provisional Pat. App. No. 63/010,863 filed Apr. 16, 2020, titled "A Fault-tolerant Grid Frequency Measurement Algorithm During Transients" which is incorporated by reference.

STATEMENT REGARDING FEDERALLY SPONSORED RESEARCH AND DEVELOPMENT

This invention was made with government support under Contract No. DE-AC05-00OR22725 awarded by the United States Department of Energy. The government has certain rights in the invention.

BACKGROUND

Technical Field

This application relates to electric girds, and more specifically to electric grid frequency measurements.

Related Art

Many grid parameter estimation processes measure electricity under steady-state and dynamic conditions. They do not perform accurate grid measurements during transient conditions. In some power grid events, a phase angle jump causes waveform discontinuity, causing the existing estimation algorithms to fail as the estimation assumes that the waveform is continuous. Measurement errors that occur during system transient faults like a phase-jump are often ignored. Further, some IEEE standards do not require certified processes to account for these faults. As a result, some instruments in compliance with IEEE standards do not accurately measure electrical signals during system transient events.

DETAILED DESCRIPTION OF THE PREFERRED EMBODIMENTS

Fault-tolerant measurement systems provide reliable grid measurements during system transient events. The systems consume minimal power. Some are integrated into or are a unitary part of other monitoring and/or remediating systems and enhance monitoring algorithms. Exemplary algorithms include Discrete Fourier Transform (DFT) frequency-measurement algorithms, Phase-Locked Loop (PLL) frequency-measurement algorithms, and model-based frequency-measurement algorithms. The fault-tolerant measurement technology provides reliable measurements that may be used for electrical grid controls under steady-state and transient conditions.

The fault-tolerant measurement systems provide reliable measurements and frequency regulation to other resources too including distributed energy resources (DERs). DERs that are physical and virtual hardware and software deployed across the electrical grid, typically close to a load, and more typically behind a voltage and current meter, which can be used individually or in an aggregate (e.g., in bulk) to provide functionality and/or information to the distribution grid, customers, and/or bots. The disclosed fault-tolerant measurement systems may integrate with or comprise a unity part of protection relays, DER devices, Phasor Measurement Units (PMUs), smart meters, wind turbines, energy storage units, digital fault detectors, power quality analyzers and/or any combination of these and other systems.

Figure 1:
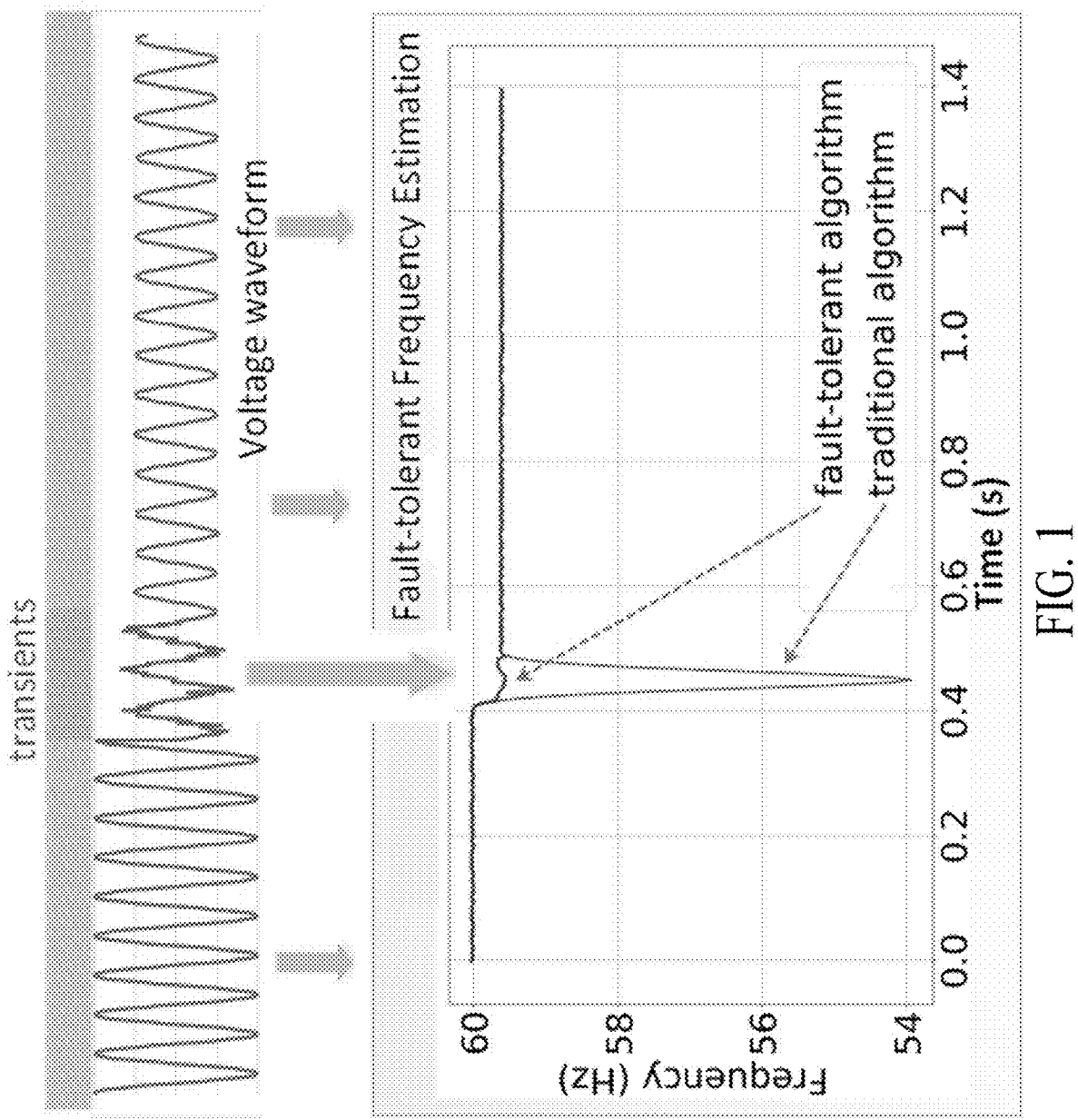
FIG. 1 illustrates a fault-tolerant frequency measurement.

FIG. 1 illustrates an exemplary fault-tolerant frequency measurement positioned above a traditional frequency measurement. As shown, known measurements do not tolerate signal transient distortions as they do not discern or adapt to them. The disclosed fault tolerant frequency measurement systems detect and adapt to transient signals through a two stage approach that includes a transient fault detector 202 (also referred to as a fault detector and transient detector) and an adaptive frequency estimator 204 shown in FIG. 2. The transient fault detector 202 and the adaptive or intelligent frequency estimator (also referred to as an adaptive frequency estimator 204 and a frequency estimator) compensate for distortions by detecting transient events and adapting to them as they monitor signals continuously in a first-in first-out sequence.

Figure 2:
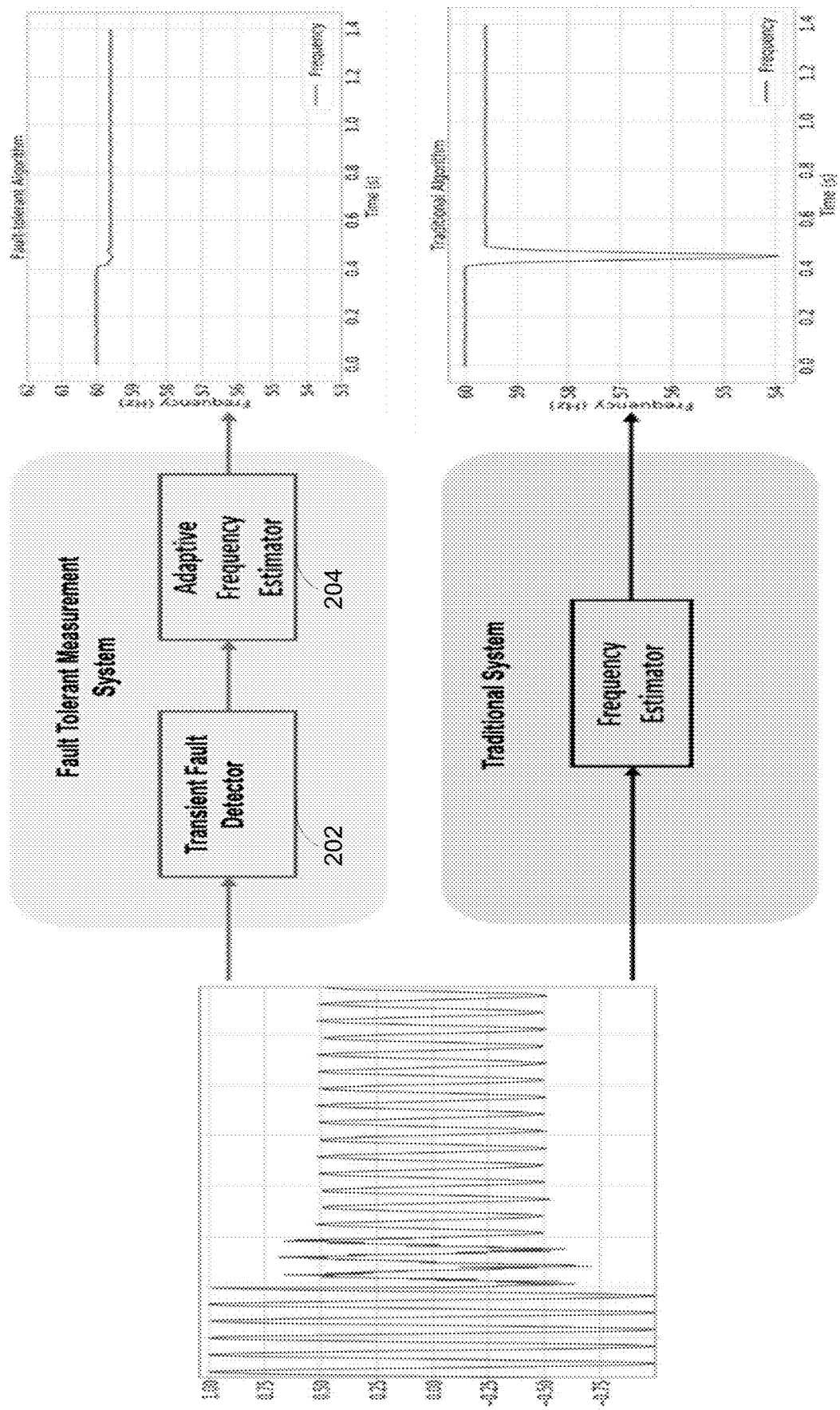
FIG. 2 is a comparison of the fault-tolerant measurement system to a traditional system.

A transient event is a short-lived burst or draw of energy caused by a sudden change of state. The source or drain of transient energy may be an internal event or an external event that may inject power into a distribution line or draw excessive power from it. The energy events couple other parts of the systems the energy serves, typically appearing as a short bursts of oscillations or discontinuities that may be caused by short or open circuits that can damage systems. Some systems include a real-time transient detector 202 that detects the magnitude change and tracks the duration of the transient events. Real-time transient detectors 202 continuously process and update measurement information at the same rate as the transient detectors receive the electrical line monitoring data. The transient detectors 202 enable the adaptive frequency estimators 204 to accurately adapt and measure monitored signals. The systems operate in real time. In FIG. 2, the adaptive frequency estimator 204 adjusts its estimation window function referred to as a window (e.g., increases in width or decreases in width) in response to the detection and duration of a distortion event to minimize estimation errors. The detected discontinuities may include one or more phase jumps and/or one or more magnitude level changes, jumps, or variations such as those caused by voltage sags and/or swells. A voltage sag may be caused by line faults (e.g., such as a three phase-to-ground fault, a single line-to-ground fault, and/or line-to-line faults) or other electrical faults that occur in one or more transmission and/or distribution systems that serve industrial, commercial, utility, and/or end users.

When a power grid operates in steady state (e.g., without a transient event), the electrical grid signals (called grid signals) are represented by equation (1)

$$x(t) = \sqrt{2} A_0 \cos(2\pi f t + \varphi) \quad (1)$$

where $A_o$ is the magnitude of the power grid signal, f is the fundamental frequency of the power grid signal, and $\varphi$ is the phase angle of the power grid signal. As the power grid operates close to a nominal frequency (e.g., 60 Hz), the voltage and current of power system are periodic and are expressed as equation $$x(t) - x(t-T) = 0 \quad (2)$$

where T is the signal period of the electrical grid signals.

When the grid experiences transient events, the grid signals become distorted and the signals become irregular and/or aperiodic. Under these conditions, $x(t) - x(t-T) \neq 0$; it is equal to alpha $x(t) - x(t-T) = \alpha$. As the deviation from the expected periodic signal increases, the absolute value of alpha $|\alpha|$ increases indicating a transient event. To account for noise, the transient fault detector 202 executes the computation expressed as equation (3).

$$\gamma(t) = |\int_{t=0}^{T} [x(t) - x(t-T)] dt| \quad (3)$$

Equation 3 represents the integration of $x(t) - x(t-T)$ over one fundamental frequency cycle of grid signals. Under steady-state grid conditions, $x(t-T)$ is substantially equal zero, making $\gamma(t)$ substantially equal to zero. In use, the grid signals are digitally sampled. If there are N samples in one fundamental frequency cycle, then the detector equation is expressed as equation 4.

$$\gamma(k) = |\Sigma_{k=0}^{N} x(k) - x(k-N)| \quad (4)$$

Figure 3:
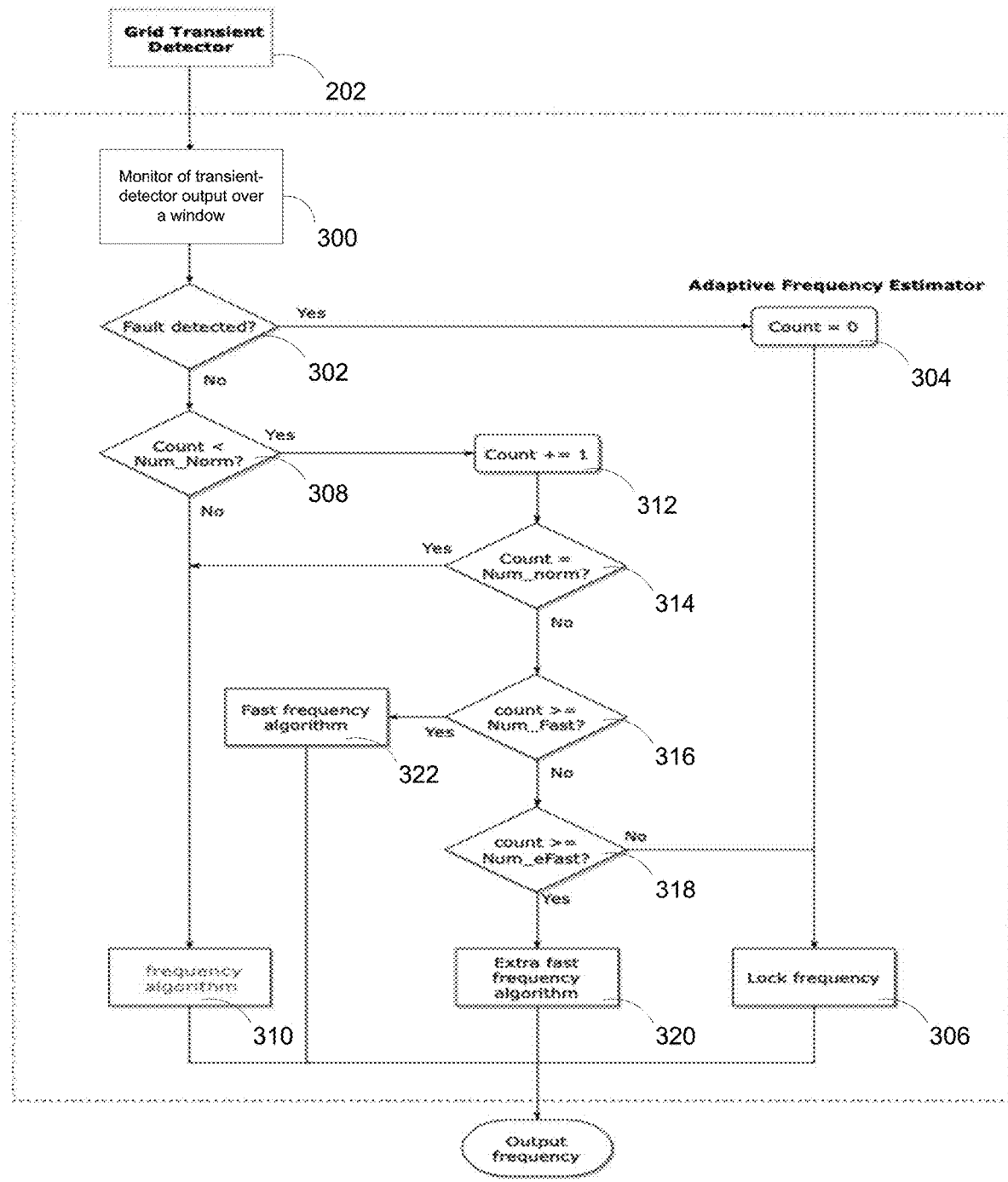
FIG. 3 is a frequency estimation algorithm executed by the adaptive frequency estimator.

FIG. 3 illustrates a frequency estimation algorithm executed by the adaptive frequency estimator 204. The estimation algorithm initiates, at 300, by monitoring an output of the transient fault detector 202 over a window. The output is down sampled, and in some applications, down sampled such that a ratio may equal to the block size of voltage or current waveforms used by frequency estimation. In a use case, the DFT-based frequency algorithm processes one cycle of voltage or current waveforms. In such case, the down sample size equal one cycle. For each cycle of waveforms, the monitoring of detector 202's output over a window, at 300, detects a fault when at least a value exceeds a predetermined threshold. When it is equal or below the predetermined threshold, a fault is not detected.

When a fault is detected at 302, the value of a counter (e.g., a count) is reset to zero at 304 and the output of adaptive frequency estimator 204 locks to the last (e.g., the most recent) frequency measurement made by the frequency estimation algorithm at 306. When a fault is not detected at 302 and the count exceeds a first predetermined state numerical count 308, the frequency estimation algorithm executes a DFT frequency-measurement, PLL frequency-measurement, a model-based frequency-measurement and/or or another frequency measurement or combinations shown as the frequency algorithm measurement at 310. Similarly, when the output of the transient fault detector 202 is below the predetermined transient threshold at 302 and an incremented count that occurs at 312 equals the first predetermined state numerical count at 314, the frequency algorithm measurement is executed at 310.

When the incremented count is not equal to the first predetermined state numerical count at 314, but is greater than or equal to a predetermined numerical fast count at 316 of FIG. 3, the adaptive frequency estimator 204 executes a fast real-time frequency estimation at 322. The fast real-time frequency estimation applies one or more frequency estimation calculations described herein by processing less cycles of the grid electrical signal than those processed by the frequency algorithm measurement at 310.

When the incremented count is not greater than or equal to a predetermined numerical fast count at 316, and is greater than or equal to a predetermined numerical extra fast count at 318, the adaptive frequency estimator 204 executes and outputs an extra fast real-time frequency estimation at 320. The extra fast real-time frequency estimation may apply the frequency estimation calculations described herein by processing even less cycles of the grid electrical signal than fast real-time frequency estimation measurement. When the incremented count is not greater than or equal to a predetermined numerical fast count at 316, and is not greater than or equal to the predetermined numerical extra fast count at 318, the adaptive frequency estimator 204 locks to the last frequency measurement made by the frequency estimation algorithm at 306.

In FIG. 3, the number of cycles processed by the adaptive frequency estimator 204 depends on the strength of the transient event. As the transient events/fault's effects continuously decay or weaken, the window size dynamically increase and the fault-tolerant measurement systems processes more cycles of the monitored grid signal. As result of variable window sizes, the fault-tolerant measurement systems provide low latency real time measurements of the grid signal following system events.

Figure 4:
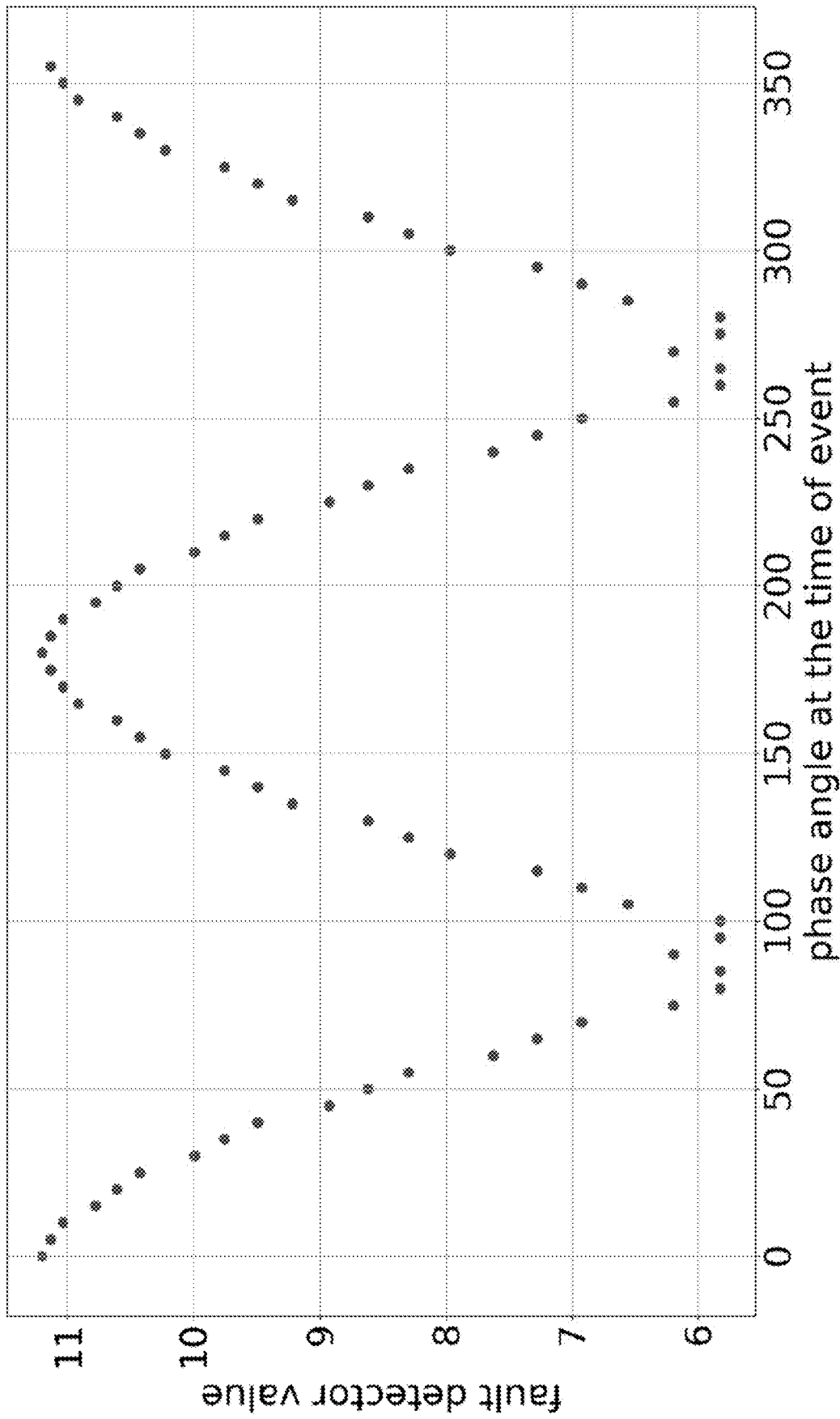
FIG. 4 shows a minimum output of a transient fault detector under different phase jump conditions.

To determine the predetermined transient threshold to be used at operation 300, different types of test signals are generated to evaluate the frequency measurement errors of the adaptive frequency estimator 204. For each test, the value $\gamma(t)$ was recorded when the frequency measurement error reaches a predetermined value such as about 0.5 Hz. FIG. 4 shows the $\gamma$ values under different test conditions. In FIG. 4, the x-axis represents the phase angle of the test signal when a phase jump event occurs. For each of the tests, a number of sub-test signals are generated with a phase angle jump from −360 to 360 degree at a step of 5 Hz. The dots shown in FIG. 4 represent a minimum value in each test. To ensure the frequency measurement errors are below 0.5 Hz under all the test cases, the predetermined transient threshold should be below the minimum under all tests. In FIG. 4, the minimum value is about 5.7, and 5 is selected as the value of the predetermined transient threshold.

Figure 5:
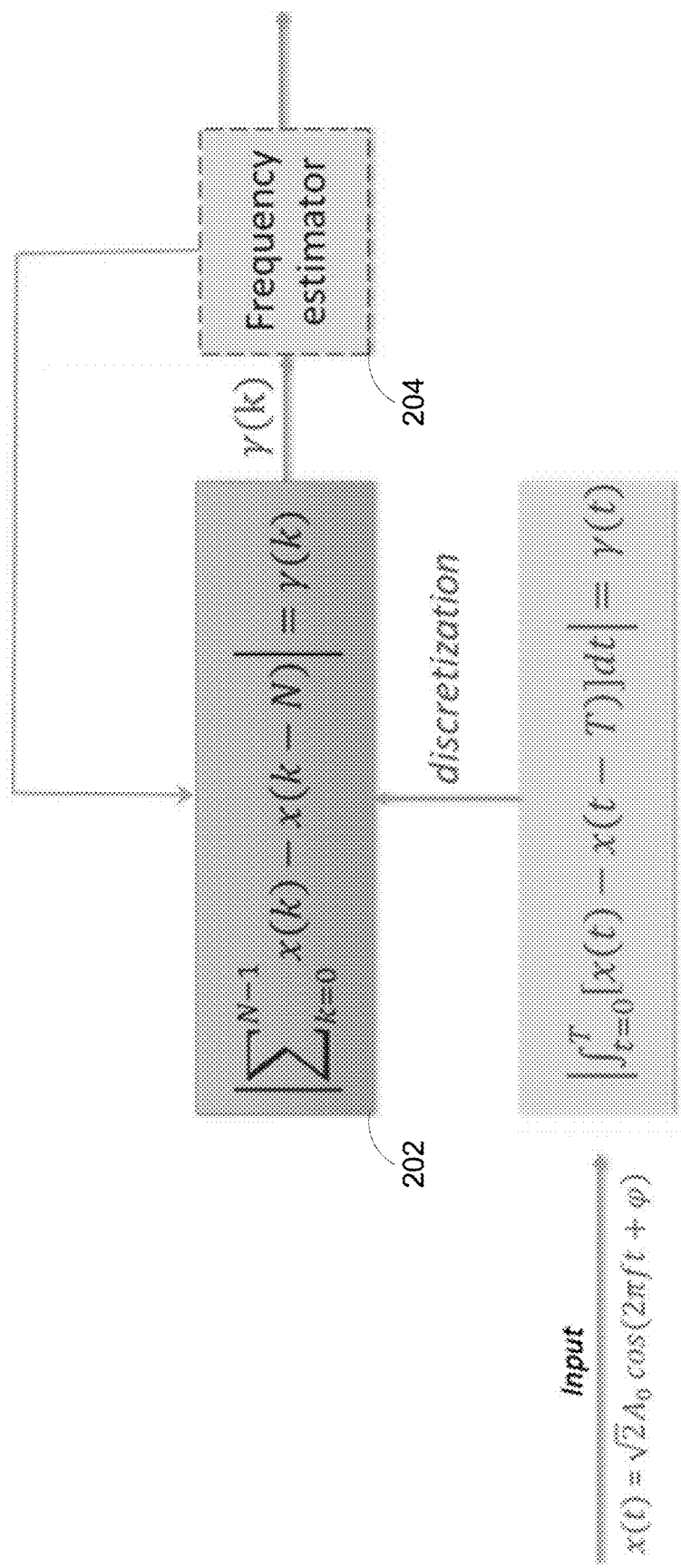
FIG. 5 is an alternate fault-tolerant measurement system.

The transient detector 202 can be implemented recursively as shown in FIG. 5. The transient detector 202 runs in real-time expressed by:

$$\gamma(i) = |\Sigma_{k=0}^{N-1} x(i+k) - x(i+k-N)| \quad (5)$$

where x is the sampled value of the power grid electric waveforms and N is the number of sampled values in one fundamental frequency cycle (e.g., 1/60 second for a 60 Hz power source) in this exemplary system. The computation time processed in equation 5 is proportional to N, which will increase with the sampling rate. Equation 5 can be implemented recursively in practical applications to minimize computation cost, which is described below.

$$s(i) = \rho_{k=0}^{N-1} x(i+k) - x(i+k-N) \quad (6)$$

which is rewritten as equation 7.

$$s(i) = \begin{cases} s(i-1) + \{x(i+N) - x(i)\} - \{x(i) - x(i-N)\}, & i > 0 \\ \sum_{k=0}^{N-1} x(k) - x(k-N), & i = 0 \end{cases} \quad (7)$$

In equation 7, the number of numerical operations that calculate s(0) is proportional to N. It requires only three mathematical operations: one addition and three subtractions. After s(0) is calculated, s(i) is recursively calculated. γ(i) is calculated from s(i). A single absolute operation is needed. This enables fault-tolerant measurement systems and the systems that are integrated with or are unitary part of systems that enable them to direct or control electrical processes as the transient events or distortions are occurring.

In equations 5-7, the variable 'N' is a multiple integer of number of samples in one grid frequency cycle. In a use case, when voltage or current waveforms sampling rate is 1440 Hz/s, and grid frequency is 60 Hz, twenty four samples in one grid frequency are sampled. In this use case, 'N' may comprise 24, 48, etc. In a use case, N equal to number of samples in one grid frequency cycle. When the grid frequency deviates from 60 Hz, for example, such as 61 Hz, for example, the number of samples in one grid frequency cycle comprises 22.95. In this exemplary use case, N comprises an integer approximation of 22.95, such as 23, for example. Overall, $$N = g\left(i * \frac{fs}{fre}\right)$$

where fs comprises the waveforms sampling rate, fre comprises the estimated frequency, and i comprises an integer of at least 1 or greater. The g(x) function truncates number x to the closet integer.

An exemplary adaptive frequency estimator 204 includes a model-based frequency-measurement algorithms or systems, or DFT frequency-measurement, for example. In a DFT application, the exemplary adaptive frequency estimator 204 computes the DFT by processing a single fundamental frequency. The time interval between two DFT is then determined by the frequency estimate rate (e.g., $X_r$ and $X_i$). When the frequency is computed every quarter cycle (1/240 seconds), the DFT is computed every quarter cycle. For each DFT, $X_r$ and $X_i$ are expressed by equation 8.

$$\begin{cases} X_r = \frac{1}{\sqrt{2}} \frac{2}{N} \sum_{k=0}^{N-1} x_k \cos\left(\frac{2\pi k}{N}\right) \\ X_i = \frac{1}{\sqrt{2}} \frac{2}{N} \sum_{k=0}^{N-1} x_k \sin\left(-\frac{2\pi k}{N}\right) \end{cases} \quad (8)$$

In FIG. 5, the cosine expression, the sine expression, and $$\frac{1}{\sqrt{2}} \frac{2}{N}$$

are constants that can be processed in advance of signal detections and measurements (e.g., preprocessed or processed offline) further reducing processor loads and real time processing times.

The phase angle relative to $X_i$ and $X_r$ is expressed by equation 9.

$$\varphi = \arctan\left(\frac{X_i}{X_r}\right) \quad (9)$$

The derivate of the phase angle derives the frequency expressed in equation 10.

$$\varphi'(m) = \frac{\varphi(m) - \varphi(m-1)}{\Delta t} = 2\pi f(m), \quad (10)$$
$$m \geq 1$$

In equation 10, m is the sequence index of the phase angle, f(m) is the estimated grid frequency, and Δt is the time interval between two phase angles. According to equation 10, the frequency can be computed by φ(m) and φ(m−1). Because power grid wave forms include disturbances such as noise, harmonics, oscillation, etc., a series of phase angles are used in many frequency estimations.

When the number of phase angles processed for a frequency estimation is (2L+1), quadratic polynomial fits the phase angles, as expressed by equation 11.

$$p(i) = \alpha_0 + \alpha_1 t(i) + \alpha_2 t(i)^2, \, i=0, \ldots, 2L \quad (11)$$

where $\alpha_0$, $\alpha_1$, $\alpha_2$ are the coefficients of the quadratic polynomial, $t(i)=(i-L)\Delta t$.

The derivate of the phase angle p(i) is expressed by equation 12.

$$p'(i) = \alpha_1 + 2\alpha_2 t(i). \quad (12)$$

Further, at sample index i=L, the derivative is simplified as expressed in equation 13.

$$p'(L) = \alpha_1. \quad (13)$$

The frequency at sample index i=L can then be expressed by equation 14.

$$f = \frac{\alpha_1}{2\pi}. \quad (14)$$

Thus, by equation 14 an estimate of $\alpha_1$ estimates the source frequency. Here, the curve fitting errors are minimized to estimate $\alpha_1$. Using an estimated phase angle φ(i) and a curve fitting p(i), the sum of the square of the error is expressed by equation 15.

$$e = \epsilon(\alpha_0, \alpha_1, \alpha_2) = \sum_{0}^{2L} (p(i) - \varphi(i))^2 \quad (15)$$

To minimize the error e, the partial derivatives of e with respect to the coefficient $\alpha_0$, $\alpha_1$, $\alpha_2$ are derived. The equation resulting from the partial derivative evaluation of the error e with respect to $\alpha_0$, $\alpha_1$, and $\alpha_2$ are expressed as follows.

$$\frac{\partial e}{\partial \alpha_0} = 2\alpha_0(2L+1) + 2\alpha_1 \sum_{i=0}^{2L} t(i) + 2\alpha_2 \sum_{i=0}^{2L} t(i)^2 - 2\sum_{i=0}^{2L} \varphi(i) \quad (16)$$

$$\frac{\partial e}{\partial \alpha_1} = 2\alpha_0 \sum_{i=0}^{2L} t(i) + 2\alpha_1 \sum_{i=0}^{2L} t(i)^2 + 2\alpha_2 \sum_{i=0}^{2L} t(i)^3 - 2\sum_{i=0}^{2L} \varphi(i)t(i) \quad (17)$$

$$\frac{\partial e}{\partial \alpha_2} = 2\alpha_0 \sum_{i=0}^{2L} t(i)^2 + 2\alpha_1 \sum_{i=0}^{2L} t(i)^3 + 2\alpha_2 \sum_{i=0}^{2L} t(i)^4 - 2\sum_{i=0}^{2L} \varphi(i)t(i)^2 \quad (18)$$

To minimize the error e, the derivatives are set equal to zero $$\left(\text{i.e. } \frac{\partial e}{\partial \alpha_0} = \frac{\partial e}{\partial \alpha_1} = \frac{\partial e}{\partial \alpha_2} = 0\right),$$

thus, $$\begin{bmatrix} (2L+1) & \sum_{i=0}^{2L} t(i) & \sum_{i=0}^{2L} t(i)^2 \\ \sum_{i=0}^{2L} t(i) & \sum_{i=0}^{2L} t(i)^2 & \sum_{i=0}^{2L} t(i)^3 \\ \sum_{i=0}^{2L} t(i)^2 & \sum_{i=0}^{2L} t(i)^3 & \sum_{i=0}^{2L} t(i)^4 \end{bmatrix} \begin{bmatrix} \alpha_0 \\ \alpha_1 \\ \alpha_2 \end{bmatrix} = \begin{bmatrix} \sum_{i=0}^{2L} \varphi(i) \\ \sum_{i=0}^{2L} \varphi(i) t(i) \\ \sum_{i=0}^{2L} \varphi(i) t(i)^2 \end{bmatrix}. \quad (19)$$

Because $t(i)=(i-L)\Delta t$, $$\Sigma_{i=0}^{2L} t(i) = \Sigma_{i=0}^{2L} t(i)^3 = 0. \quad (20)$$

equation 20 can be expressed as equation 21.

$$\begin{bmatrix} (2L+1) & 0 & \sum_{i=0}^{2L} t(i)^2 \\ 0 & \sum_{i=0}^{2L} t(i)^2 & 0 \\ \sum_{i=0}^{2L} t(i)^2 & 0 & \sum_{i=0}^{2L} t(i)^4 \end{bmatrix} \begin{bmatrix} \alpha_0 \\ \alpha_1 \\ \alpha_2 \end{bmatrix} = \begin{bmatrix} \sum_{i=0}^{2L} \varphi(i) \\ \sum_{i=0}^{2L} \varphi(i) t(i) \\ \sum_{i=0}^{2L} \varphi(i) t(i)^2 \end{bmatrix} \quad (21)$$

Simplifying the equation renders equation 22.

$$T\alpha = \varphi \quad (22)$$

Applying the inverse of matrix T ($T^{-1}$) to both sides of equation 22, renders equation 23.

$$\alpha = T^{-1} \varphi \quad (23)$$

Equation 23 can be expanded as expressed by equation 24.

$$\begin{bmatrix} \alpha_0 \\ \alpha_1 \\ \alpha_2 \end{bmatrix} = \begin{bmatrix} T_{11} & T_{12} & T_{13} \\ T_{21} & T_{22} & T_{23} \\ T_{31} & T_{32} & T_{33} \end{bmatrix} \begin{bmatrix} \sum_{i=0}^{2L} \varphi(i) \\ \sum_{i=0}^{2L} \varphi(i) t(i) \\ \sum_{i=0}^{2L} \varphi(i) t(i)^2 \end{bmatrix} \quad (24)$$

where $T_{ij}$ is an entry of matrix $T^{-1}$.

Because only $\alpha_1$ is processed for frequency estimation, only $T_{21}$, $T_{22}$, and $T_{23}$ in $T^{-1}$ needs to be calculated, which are expressed as follows:

$$T_{21} = -\frac{1}{\det(T^{-1})} \begin{vmatrix} 0 & \sum_{i=0}^{2L} t(i)^2 \\ 0 & \sum_{i=0}^{2L} t(i)^4 \end{vmatrix} = 0 \quad (25)$$

$$T_{22} = \frac{1}{\det(T^{-1})} \begin{vmatrix} 2L+1 & \sum_{i=0}^{2L} t(i)^2 \\ \sum_{i=0}^{2L} t(i)^2 & \sum_{i=0}^{2L} t(i)^4 \end{vmatrix} = \frac{(2L+1) \sum_{i=0}^{2L} t(i)^4 - \left(\sum_{i=0}^{2L} t(i)^2\right)^2}{\det(T^{-1})} \quad (26)$$

$$T_{23} = -\frac{1}{\det(T^{-1})} \begin{vmatrix} 2L+1 & 0 \\ \sum_{i=0}^{2L} t(i)^2 & 0 \end{vmatrix} = 0 \quad (27)$$

where $\det(T^{-1})$ is the determinant of $T^{-1}$.

Since $T_{21}=T_{23}=0$, $\alpha_1$ can be expressed by $$\alpha_1 = T_{21} \sum_{i=0}^{2L} \varphi(i) = T_{22} \sum_{i=0}^{2L} \varphi(i) t(i) + T_{23} \sum_{i=0}^{2L} \varphi(i) t(i)^2 = T_{22} \sum_{i=0}^{2L} \varphi(i) t(i). \quad (28)$$

Because $T_{22}$ only depends on the parameters of L and $\Delta t$, which are constant parameters, $T_{22}*t(i)$ can be processed in advance of signal detections and measurements (e.g., pre-processed or processed offline) further reducing processor loads.

By equations 14 and 28, frequencies can be estimated using a total number of (2L+1) phase angles. The processing time of the measured frequency estimation is proportional to L since it requires (2L+1) multiplications and 2L additions according to equation 27. In practice, the phase angle obtained by equation 9 is between $-\pi$ to $\pi$. Thus, the angles may need to be unwrapped by a least squares fitting.

The computation utilization rate of the frequency estimation on the DSP occurs at a very minimal load. This characteristic assures that the disclosed fault-tolerant measurement systems detect and adapt to transient signals and other distortions. The transient fault detector 202 operating at a sampling rate of 6000 Hz generally needs five numerical operations per measurement, that takes six thousand measurements per second and executing thirty-thousand numerical operations per second, that can be executed easily on a one-hundred and fifty million MFLOPS (Million Floating Point Operations Per Second) DSP (Digital Signal Processor). Similarly, the computation utilization rate of the adaptive frequency estimator 204 operating under the same conditions generally computes two-hundred and ninety five numerical operations per measurement, that takes two-hundred and forty measurements per second executing seventy-thousand eight hundred numerical operations per second, that could be also easily executed on a one-hundred and fifty million MFLOPS. The transient fault detector 202 and adaptive frequency estimator 204 operates at a very low computational cost for many processors.

Another exemplary alternative systems or apparatuses for determining in real time frequency of grid signals x(t) corresponding to an electrical grid includes a transient detector and frequency estimator. The transient detector receive a grid signal x(k) from a voltage meter or current meter connected to the electrical grid, where the monitored signal is a periodic signal with a nominal frequency $f_0$ and has a sampling rate $$\frac{1}{\Delta t}.$$

The transient detector produces, in real time and at the sampling rate of the monitored signal, a deviation signal $x_{dev}$ indicative of whether or not the monitored signal is periodic. It determines, over one or more cycles, a measurement signal γ corresponding to the deviation signal. The frequency estimator is communicatively linked with the transient detector 202. The frequency estimator 204 determines a frequency signal $f_e$ that corresponds to an estimated frequency of the monitored signal by using a frequency-estimation method such as those described herein while values of the measurement signal (γ) are less than a predetermined transient threshold (thr) also referred to as the deviation threshold that can be expressed as γ<thr. The frequency estimator 204 maintains the frequency signal at a constant value while values of the measured signal equals or exceeds the deviation threshold as expressed by γ≥thr. In some systems, the transient detector is configured to determine the measurement signal by integrating the signal over one or more monitored signal cycles. The integration expressed in equation 30 removes signal noise and other disturbances. Here, k is a sample index, and N is the number of sampled values in one or more cycles.

$$\gamma(t) = |\textstyle\sum_{n=0}^{N-1}((x_{dev}(k+n))| \qquad (30)$$

In some of the other exemplary alternative systems or apparatuses, the transient detector 202 sets or transmits a flag (e.g., a value that signals information to the frequency estimator 204) to the frequency estimator 204 indicating that the grid signal remains periodic when values of the measurement signal are less than the deviation threshold (γ<thr) and exhibits a transient when values of the measurement signal equal or exceed the deviation threshold (γ≥thr). In these systems, a transient event may comprise a phase angle jump and/or a magnitude jump. Exemplary frequency-estimation processes used to determine the frequency signal while values of the measurement signal are less than the deviation threshold may include a DFT based frequency-measurement process/algorithm, and/or a model-based frequency-measurement process/algorithm. The monitored signals include single-phase grid signal and/or three-phase grid signals. The other exemplary alternative systems may be integrated in or are a unitary part of a protection relay, a DER device, a PMU, a smart meter, a digital fault detector, and/or a power quality analyzer.

The disclosed transient detector and/or frequency estimator is integrated with or comprises a unitary part of a solar inverter, a power generator, a wind turbine, and/or a Flexible Alternating Current Transmission System (FACTS) in alternate systems. Some alternate systems are implemented as instructions encoded in memory and/or implemented in circuitry such as an application integrated circuit. Some circuitry systems include receiver circuitry coupled to a voltage meter and/or a current meter connected to an electrical grid. The receiver circuitry receives monitored grid signals measured from the electrical grid. Transient detector circuitry comprising some or all of the processes and structures described herein that detect transients and/or distortions communicates with the receiver circuitry. The frequency estimator circuitry comprising some or all of the processes and structures described herein that compensates for those distortions and transients and adapts to them, communicates with the receiver circuitry, and transmitter circuitry. The frequency estimator circuitry communicates with electrical-grid protection and/or mediation devices through the transmitter circuitry.

Figure 6:
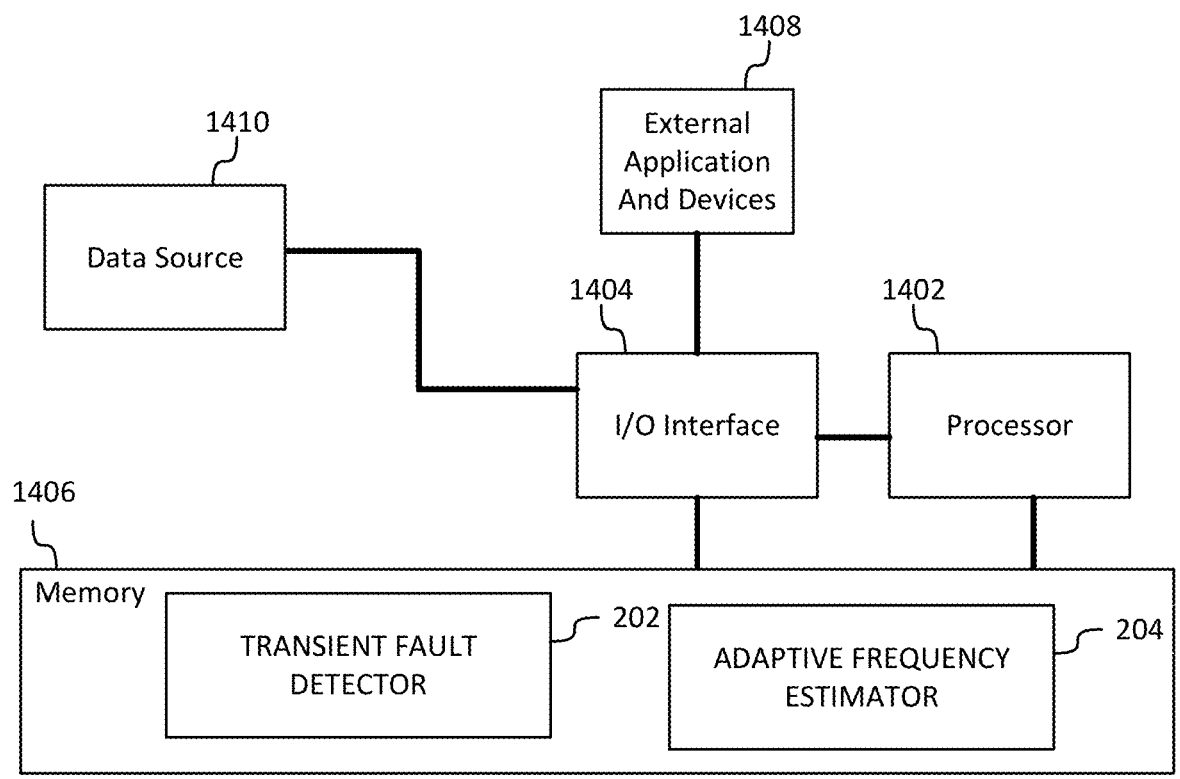
FIG. 6 is another alternate fault-tolerant measurement system.

FIG. 6 is a block diagram of an alternate fault-tolerant measurement systems that represents the systems and processes shown FIGS. 1-5. The system comprises a processor 1402 and a non-transitory media such as a non-volatile memory (the contents of which are accessible by the processors) or an application-specific integrated circuit. The I/O interface 1404 connects devices and local and/or remote applications such as, for example, additional local and/or remote monitored electrical sources and devices. The I/O interface 1404 also connects to other data sources 1410. The memory 1406 stores instructions, which when executed the processor 1402 causes the fault-tolerant measurement systems to render some or all of the functionality associated with detecting and compensating for distortions and transient events and adapting voltage and/or current measurements. The memory 1406 stores instructions, which when executed by the processor 1402, causes the fault-tolerant measurement systems to render functionality associated with the transient fault detector 202 and the adaptive frequency estimator 204.

Figure 7:
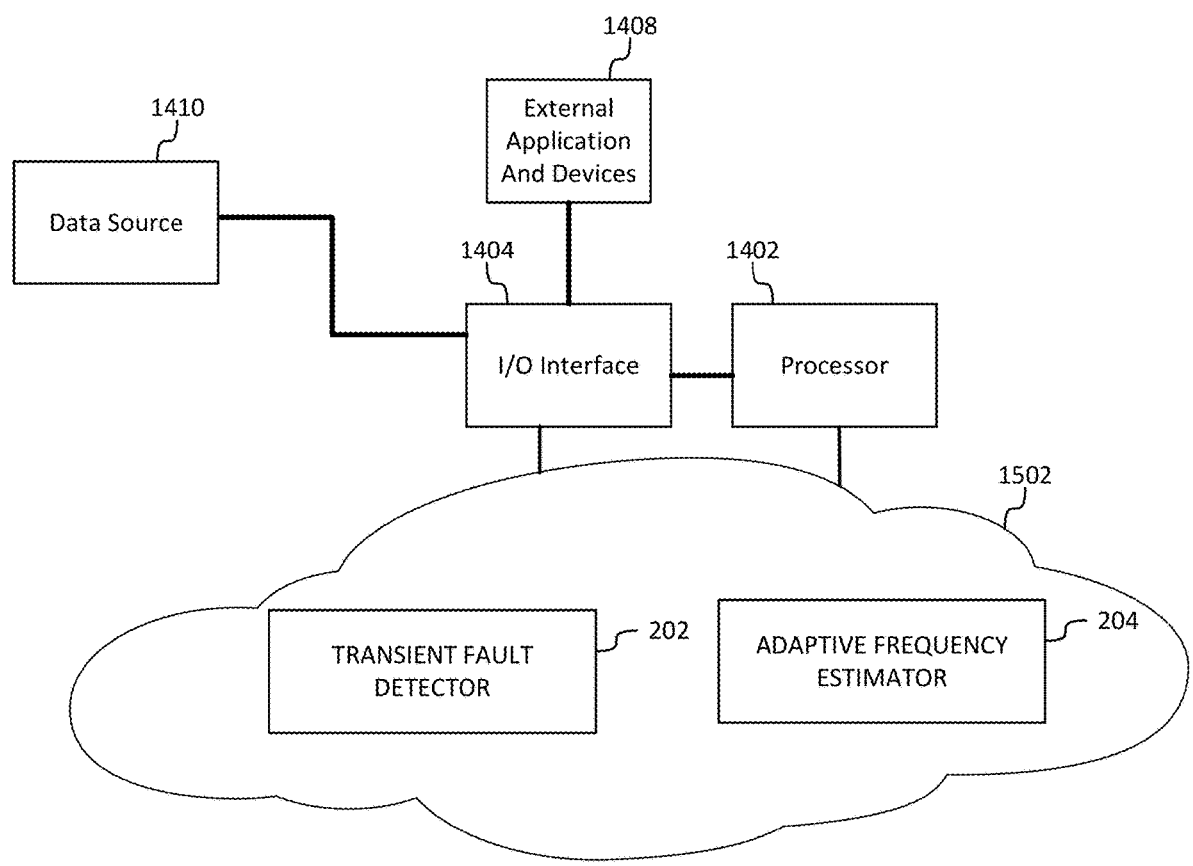
FIG. 7 is another alternate fault-tolerant measurement system.

In yet another alternate fault-tolerant measurement systems, the non-transitory media provided functionality is provided entirely or partially through cloud storage and services 1502 as shown in FIG. 7. In these fault-tolerant measurement systems, cloud storage and services provides ubiquitous access to fault-tolerant measurement system's resources and higher-level services that can be rapidly provisioned over one or more network. Cloud storage and services 1502 allows for the sharing of resources to achieve coherence services across many devices at many locations across many electrical grids and provides economies of scale.

The processors 1402 may comprise a single processor or multiple processors that may be disposed on a single chip, on multiple devices, or distributed over more than one system. The processors 1402 may be hardware that executes computer executable instructions or computer code embodied in the memory 1406 or in other memory to perform one or more features of the systems described herein. The processor 1402 may include a central processing unit (CPU), a graphics processing unit (GPU), an application specific integrated circuit (ASIC), a DSP, a field programmable gate array (FPGA), a digital circuit, an analog circuit, a microcontroller, any other type of processor, or any combination thereof.

The memory 1406 and/or storage disclosed may retain an ordered listing of executable instructions for implementing the functions described above in a non-transitory computer code. The machine-readable medium may selectively be, but not limited to, an electronic, a magnetic, an optical, an electromagnetic, an infrared, or a semiconductor medium. A non-exhaustive list of examples of a machine-readable medium includes: a portable magnetic or optical disk, a volatile memory, such as a Random Access Memory (RAM), a Read-Only Memory (ROM), an Erasable Programmable Read-Only Memory (EPROM or Flash memory), or a database management system. The memory 1406 may comprise a single device or multiple devices that may be disposed on one or more dedicated memory devices or disposed on a processor or other similar device. An "engine" comprises a processor or a portion of a program executed by the processor that automatically executes or supports the detecting, measuring, compensating, and adapting to transient events. It describes a special-purpose program that use models, DFTs, and/or deliver resources. When functions, steps, etc. are said to be "responsive to" or occur "in response to" another function or step, etc., the functions or steps necessarily occur as a result of another function or step, etc. It is not sufficient that a function or act merely follow or occur subsequent to another. The term "substantially" or "about" may encompass a range that is largely, but not necessarily wholly, what is specified. It encompasses all but an insignificant amount, such as a variance within a range of five or ten percent of the given value.

The systems illustratively disclosed herein suitably may be practiced in the absence of any element (including hardware and/or software), which is not specifically disclosed herein. They may operate in the absence of those elements. Further, the various elements described in each of the many systems described herein is regarded as divisible with regard to the individual elements described, rather than inseparable as a whole. In other words, alternate systems encompass any variation and combinations of elements described herein and may be made or used without the various elements described (e.g., they may operate in the absence of one or more of the elements disclosed herein and/or shown in FIGS. 1-7). Fault-tolerant measurement systems provide reliable grid measurements during system transient faults. The systems consume minimal power and are easily integrated into or formed unitary with other electrical-grid protection and remediation systems. The fault-tolerant measurement technology provides reliable measurements that may be used for electrical grid controls under steady-state and transient conditions.

The fault-tolerant measurement systems provide reliable measurements and frequency regulation to other resources. The resources are physical and virtual hardware and software deployed across the electrical distribution grid, and in some applications, close to a load, which can be used individually or in a bulk. The systems may integrate with or are a unity part of any electrical-grid protection and/or remediating device.

Other systems, methods, features and advantages will be, or will become, apparent to one with skill in the art upon examination of the figures and detailed description. It is intended that all such additional systems, methods, features and advantages be included within this description, be within the scope of the disclosure, and be protected by the following claims.

What is claimed is:

1. An apparatus that determines in real time frequency of grid signals x(t) corresponding to an electrical grid comprising:
   a transient detector configured to:
      monitor a signal indicative of a grid signal x(k) from a voltage meter or current meter connected to the electrical grid, where the grid signal is expected to include a periodic signal with a nominal frequency $f_o$ and a sampling rate $f_s$;
      produce, in real time and at the sampling rate of the monitored signal, a deviation signal $X_{dev}$ indicative of whether or not the monitored signal includes the periodic signal; and
      determine, over one or more cycles, a measurement signal corresponding to the deviation signal; and
   a frequency estimator communicatively linked with the transient detector, the frequency estimator configured to:
      determine a frequency signal fe that corresponds to a frequency estimation of the monitored signal while values of the measurement signal are less than a deviation threshold; and
      maintain the frequency signal at a constant value while values of the measured signal equal or exceed the deviation threshold;
   where the transient detector is configured to transmit a flag to the frequency estimator indicating that the monitored signal:
      comprises a periodic signal when values of the measurement signal are less than a deviation threshold expressed as $\gamma$<thr, where $\gamma$ comprises a measurement of the deviation signal and thr comprises the deviation threshold; and
      exhibits a transient when values of the measurement signal equal or exceed the deviation threshold expressed as $\gamma \geq$thr.

2. The apparatus of claim 1, where the transient detector is configured to determine the measurement signal by integrating the deviation signal over one or more monitored signal cycles.

3. The apparatus of claim 2, where integrating the deviation signal over one or more cycles is executed according to:

$$\gamma(k) = \left| \sum_{n=0}^{N-1} (x_{dev}(k+n)) \right|$$

where $\gamma$ comprises the measurement of the deviation signal, k is a sample index, and N is a number of sampled values in one or more cycles that varies with estimated grid frequency.

4. The apparatus of claim 1, where the flag is transmitted in response to a transient event comprising a phase angle jump and/or a magnitude jump.

5. The apparatus of claim 1, where the deviation signal comprises $x_{dev}(k)=x(k+n)-x(k)$, where k is a sample index, and N is a number of sampled values in one or more cycles that varies with estimated grid frequency.

6. The apparatus of claim 1, where the frequency estimation that determines the frequency signal while values of the measurement signal are less than the deviation threshold comprises one of at least:
   a discrete Fourier transform-based frequency-measurement algorithm; or
   a model-based frequency-measurement algorithm.

7. The apparatus of claim 1, where the grid signal comprises a single-phase grid signal or a three-phase grid signal.

8. The apparatus of claim 1, where the transient detector and the frequency estimator comprises a unitary part of:
   a protection relay,
   a distributed energy resources (DER) device,
   a phasor measurement unit (PMU),
   a smart meter,
   a digital fault detector, or
   a power quality analyzer.

9. The apparatus of claim 1, where the transient detector and the frequency estimator comprises a unitary part of:
   a solar inverter;
   a power generator;
   a wind turbine; or
   a flexible alternating current transmission system.

10. The apparatus of claim 1, where the transient detector and the frequency estimator comprise a plurality of software instructions stored on a non- transitory computer-readable medium executed by a processor.

* * * * *

UNITED STATES PATENT AND TRADEMARK OFFICE
CERTIFICATE OF CORRECTION

PATENT NO. : 11,882,889 B2
APPLICATION NO. : 17/204494
DATED : January 30, 2024
INVENTOR(S) : Lingwei Zhan et al.

Page 1 of 1

It is certified that error appears in the above-identified patent and that said Letters Patent is hereby corrected as shown below:

On the Title Page

In item (73) after Assignee: UT-Battelle, LLC, Oak Ridge, TN (US) insert --University of Tennessee Research Foundation, Knoxville, TN (US)--

Signed and Sealed this
First Day of April, 2025

Coke Morgan Stewart
*Acting Director of the United States Patent and Trademark Office*